United States Patent

Isogai et al.

[11] Patent Number: 5,909,268
[45] Date of Patent: Jun. 1, 1999

[54] ALIGNMENT DETECTING APPARATUS

[75] Inventors: Naoki Isogai, Nishio; Koki Kato; Nobuharu Kobayashi, both of Gamagori; Mitsuhiro Gono, Toyokawa; Noriyuki Ishihara, Gamagori, all of Japan

[73] Assignee: Nidek Co., Ltd., Aichi, Japan

[21] Appl. No.: 08/958,158

[22] Filed: Oct. 27, 1997

[30] Foreign Application Priority Data

Oct. 25, 1996 [JP] Japan .................................. 8-300959

[51] Int. Cl.[6] ...................................................... A61B 3/14
[52] U.S. Cl. ............................................................ 351/208
[58] Field of Search ..................................... 351/205, 206, 351/208, 211, 212, 221, 246, 247

[56] References Cited

U.S. PATENT DOCUMENTS

| | | | |
|---|---|---|---|
| 4,591,247 | 5/1986 | Kamiya et al. | 351/211 |
| 4,707,090 | 11/1987 | Humphery | 351/211 |
| 5,247,341 | 9/1993 | Kurachi et al. | |
| 5,406,076 | 4/1995 | Mimura et al. | |
| 5,463,430 | 10/1995 | Isogai et al. | |
| 5,500,697 | 3/1996 | Fujieda | |
| 5,562,656 | 10/1996 | Sumiya | |

FOREIGN PATENT DOCUMENTS

| | | |
|---|---|---|
| 1-19896-B2 | 4/1989 | Japan . |
| 5-23302 | 2/1993 | Japan . |
| 6-7292 | 1/1994 | Japan . |
| A-6-85902 | 3/1994 | Japan . |
| A-6-311965 | 11/1994 | Japan . |
| 07299037 | 11/1995 | Japan . |

Primary Examiner—George Manuel
Attorney, Agent, or Firm—Oliff & Berridge, PLC

[57] ABSTRACT

An alignment detecting apparatus for detecting an alignment condition between an eye to be examined having approximately spherical surface or approximately toric surface and a device having a standard axial lines the apparatus comprising a target projecting optical system which includes a first target projecting optical system for projecting a first target with a predetermined angle relative to the standard axial line, and a second target projecting optical system for projecting a second target with a different angle compared with the angle of the first target projecting optical system relative to the standard axial lines of which at least one between the first and second targets is a target of a finite distances a detecting optical system for detecting positions of images of the first and second targets which are projected onto the eye by the first and second target projecting optical systems, and a judging device for judging the alignment condition based on results detected by the detecting optical system.

25 Claims, 9 Drawing Sheets

CORNEA RADIUS : Rc = 7.8 (mm)
DISTANCE FROM THE STANDARD POINT TO THE TARGET
    : d (STANDARD DISTANCE d0 = 40 (mm))
HEIGHT DISTANCE FROM THE OPTICAL AXIS OF THE TARGET : Ys
HEIGHT OF CORNEAL REFLEX : h (HEIGHT OF CORNEAL REFLEX
AT STANDARD POINT : h0)

$\dfrac{a}{b} > S$ $\dfrac{a}{b} < S$ $\dfrac{a}{b} = S$

ALIGNMENT DETECTING APPARATUS

BACKGROUND OF THE INVENTION

1. Field of the Invention

The present invention relates to an alignment detecting apparatus, and more particularly, to the apparatus for detecting an alignment condition between an eye to be examined having such reflecting surface that is approximately spherical surface or approximately toric surface, and a measuring system or the like.

2. Description of Related Art

As an examination apparatus for examining the optical characteristics of an eye to be examined, there is conventionally an ophthalmic apparatus such as a refractive power measuring apparatus (refractometer), a corneal shape measuring apparatus (keratometer) and the like. As a detecting mechanism for an alignment condition of the ophthalmic apparatus, such mechanism is known that utilizes an image of the eye which is displayed on TV monitor for observation, and a corneal reflex (a image by corneal reflection) which is formed on the eye by projecting an alignment target. The alignment is performed by adjusting the vertical and lateral directions so that the corneal reflex may be a predetermined positional relationships relative to a reticle on the TV monitor, then by adjusting the working distance (forward and backward) so that the corneal reflex may be brought into focus while observing the corneal reflex which is displayed on the TV monitor.

Referring to above-mentioned alignment detection, an adjustment of a vertical and lateral directions can be performed easily, however, in the case of adjusting a direction of working distance, it is difficult to determine a direction where the point is moved in order to bring into focus.

Therefore, as an alignment detecting mechanism in a direction of working distance, such apparatus is proposed that judges an alignment condition by projecting an alignment light bundle from an oblique direction relative to the eye, then detecting a light bundle reflected by a corneal vertex with photo-receiving elements which are disposed on symmetric optical axes with putting an optical axis in a measuring optical system therebetween.

However, above-mentioned detecting mechanism has such disadvantages that the optical system thereof become complicated since the detecting mechanism needs exclusive optical systems which choose between an alignment light bundle for detecting a working distance and an alignment light bundle for detecting the vertical and lateral directions respectively, then detects each light bundle respectively.

Also, such detecting mechanism in a direction of working distance mentioned above has such disadvantage that an alignment detecting area is small.

SUMMARY OF THE INVENTION

The present invention has been made in view of the above circumstances and has an object to overcome the above problems and to provide an alignment detecting apparatus, which has a simple configurations and by which an alignment in a direction of working distance can be performed easily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present inventions as embodied and broadly described herein, an alignment detecting apparatus for detecting an alignment condition between an eye to be examined having such reflecting surface that is approximately spherical surface or approximately toric surface, and a device having a standard axial line, the apparatus comprises a target projecting optical system which includes a first target projecting optical system for projecting a first target with a predetermined angle relative to means standard axial line, and a second target projecting optical system for projecting a second target with a different angle compared with the angle of means first target projecting optical system, relative to means standard axial line, of which at least one between means first and second targets is a target of a finite distance, a detecting optical system for detecting positions of images of means first and second targets which are projected onto the eye by means first and second target projecting optical systems, and a judging means for judging the alignment condition based on results detected by means detecting optical system.

According to the present invention, it is capable of detecting an alignment condition precisely with a simple configuration. Thereby the apparatus can be provided economically.

BRIEF DESCRIPTION OF THE DRAWINGS

The accompanying drawings, which are incorporated in and constitute a part of this specification, illustrate embodiments of the present invention and, together with the descriptions serve to explain the objects, advantages and principles of the invention. In the drawings.

DETAILED DESCRIPTION OF THE PREFERRED EMBODIMENTS

A detailed description of one preferred embodiment of an alignment detecting apparatus embodying the present invention will now be given referring to the accompanying drawings making a point of a refractive power measuring apparatus as an example.

Whole schematic configuration

Figure 1:
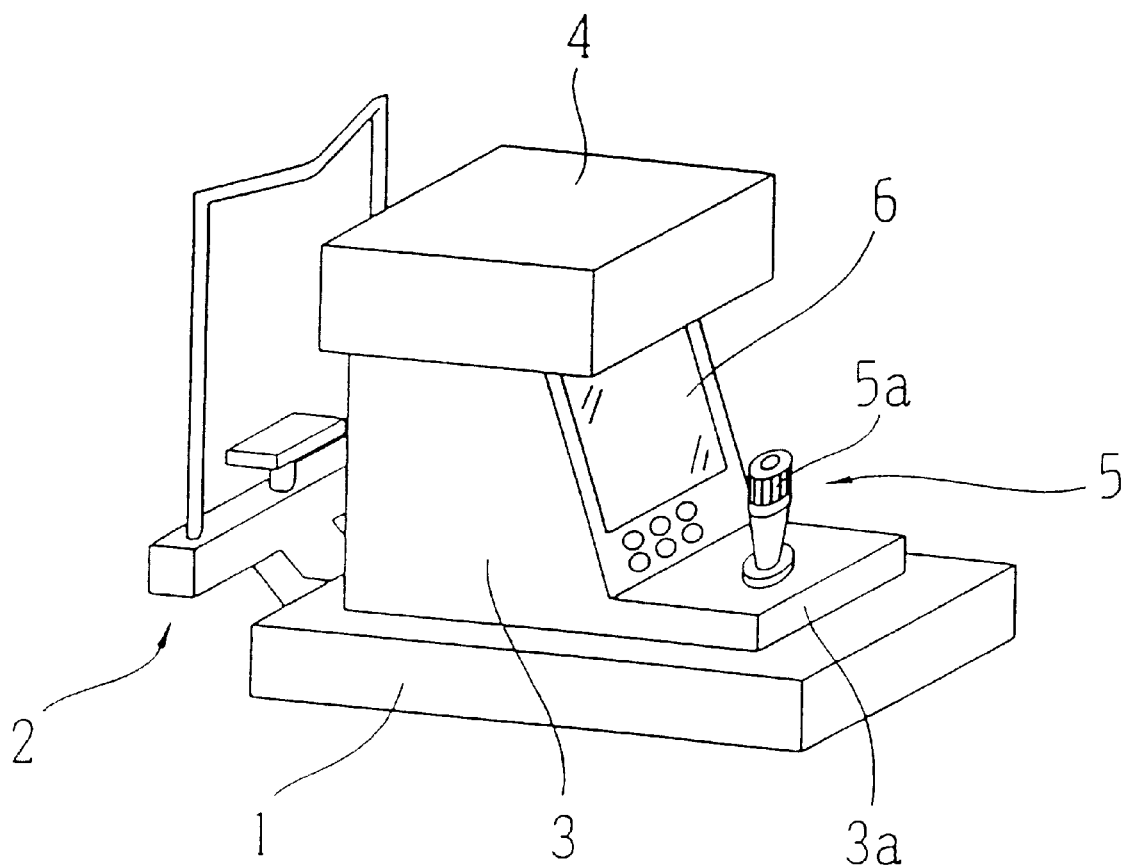
FIG. 1 is an overview of the preferred embodiment of the present inventions

FIG. 1 shows an overview of the preferred embodiment of the present invention. Reference numeral 1 is a base to which a chin rest 2 which is utilized for fixing an eye to be examined is fixed. 3 is a body, 4 is a measuring part which holds optical systems mentioned-below 5 is a joystick which is utilized for moving the body 3 and the measuring part 4, the body 3 moves and slides on a horizontal surface of the base 1 in lateral, forward and backward directions, and the measuring part 4 moves in vertical direction relative to the body 3 (concerning mechanism of joystick, see U.S. Pat. No. 5,406,076 corresponding to Japanese Patent Laid Open HEI6-7292.).

Optical systems

Figure 2:
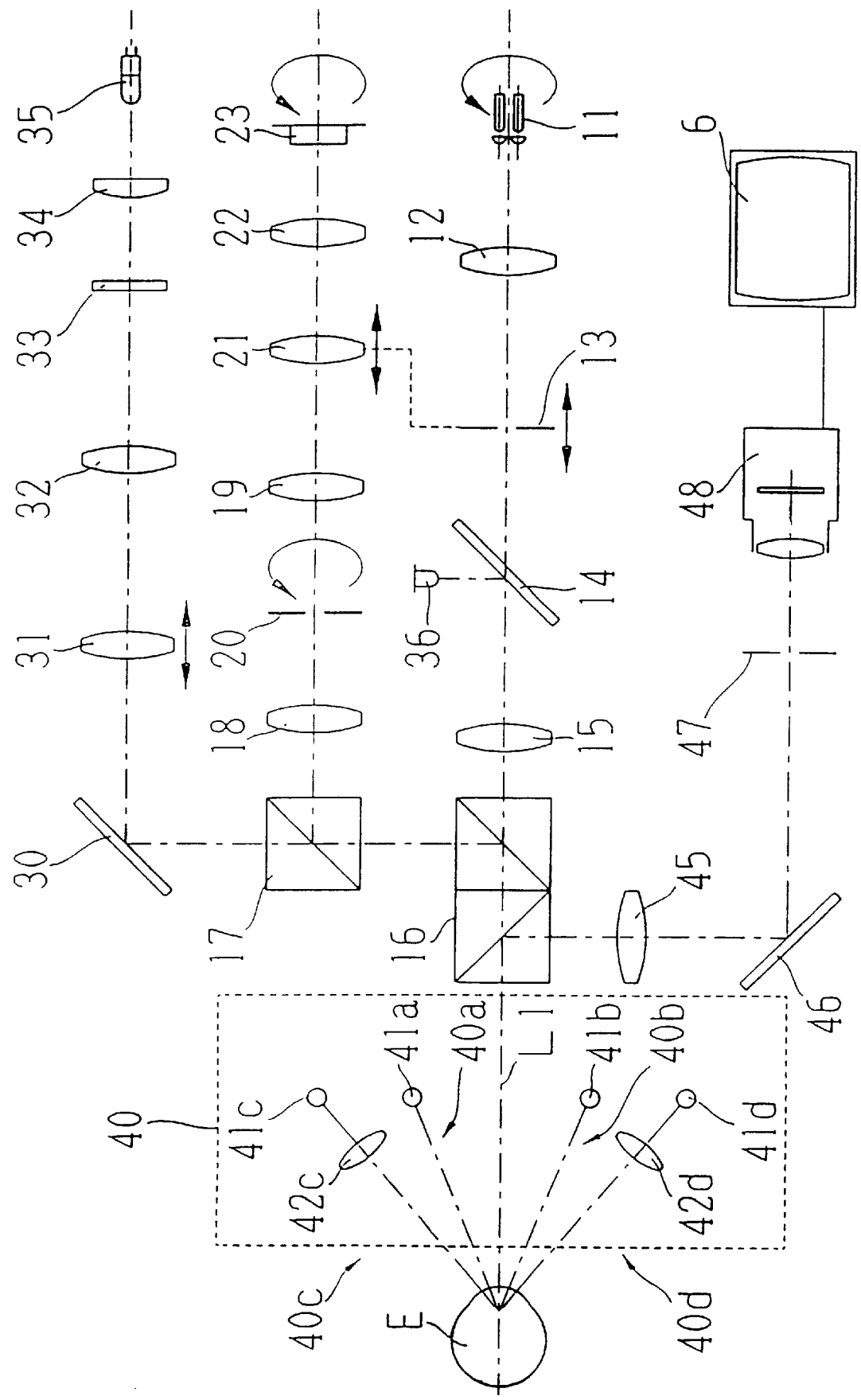
FIG. 2 is a top view showing a schematic arrangement of an optical system of the preferred embodiment of the present invention

FIG. 2 is a top view showing a schematic arrangement of an optical system of the preferred embodiment. The optical system of the apparatus will be described by dividing it into a measuring optical system, a fixation target optical system, an alignment target projecting optical system and an observing/target detecting optical system Measuring optical system Reference numeral 11 is two light sources for measurement having wavelength of infrared ranges which is disposed so as to rotate with the center at an optical axis. 12 is a collecting lens, the light sources 11s are positioned at a focusing point in front of thereat. 13 is a target plate for measurement having a target for measurement (a spot aperture), which can move so as to be disposed at a conjugate position relative to a fundus of the eye E. 14 is a beam splitter for causing an optical axis of a front target projecting optical system mentioned-below to coincide with an optical axis L1 of the measuring optical system 15 is a projecting lens which projects the target for measurement onto the fundus of the eye E.

Reference numerals 16 and 17 are beam splitters. 18 and 19 are relay lenses, 20 is a corneal reflection eliminating mask which is belt shaped and is disposed at a conjugate position relative to a cornea of the eye E, 21 is a movable lens which moves together with the target plate 13 and 22 is a focusing lens. 23 is a photo-receiving element for measurements which rotates with the center at the optical axis being synchronized with the light sources 11s and the corneal reflection eliminating mask 20.

Fixation target optical system

Reference numeral 30 is a mirror, 31 is the first relay lens capable of moving on the optical axis and fogs the eye E by moving on the optical axis. 32 is the second relay lens, 33 is a fixation target disposed at a focusing position of the second relay lens 32, 34 is a collecting lens, and 35 is an illumination lamp.

Alignment target projecting optical system

An alignment target projecting optical system consists of a front target projecting optical system which projects a target from a direction of a visual axis, and a working distance target projecting optical system which detects a working distance.

The front target projecting optical system has following configuration. Reference numeral 36 is a point light source which emits an infrared light, which is disposed at a focusing position in front of the projecting lens 15 via the beam splitter 14. A light bundle emitted from the point light source 36 is reflected by the beam splitter 14, then is made to be a parallel light bundle by the projecting lens 15 and is projected onto the eye E along the measuring optical axis L1, resulting in forming an image of a point light source 36 by corneal reflection.

The working distance target projecting optical system 40 includes two pairs of the first target projecting optical systems 40a and 40b which are disposed so as to be symmetric with putting the measuring optical axis L1 therebetween at a predetermined angle, and two pairs of the second target projecting optical systems 40c and 40d which are disposed so as to be symmetric with putting the measuring optical axis therebetween at an angle wider than the angle of the first target projecting optical systems 40a and 40b. The first target projecting optical systems 40a and 40b include a point light sources 41a and 41b which emit infrared light, and project a target of finite distance onto the eye E with a divergent light bundle. The second target projecting optical systems 40c and 40d include point light sources 41c and 41d which emit infrared lights, and collimating lenses 42c and 42d respectively, which are placed at positions being separated outer than the point light sources 41a and 41b relative to the measuring optical axis L1, and project a target of infinite distance onto the eye E. Also the target projecting optical systems 40a to 40d are disposed so as to project targets onto the same meridian in a horizontal direction relative to the eye E. Thereby, even if the eye E has corneal astigmatism, then its effect is made to be decreased so that a working distance may be detected precisely as mentioned-below.

Further, the point light sources 41a to 41d serve as illumination light sources for illuminating an anterior part of the eye E.

Observing/Target detecting optical system

A light bundle from by the anterior part of the eye E is reflected by the beam splitter 16, then is photographed by the CCD camera 48 via an objective lens 45, a mirror 46, and a telecentric aperture 47. The image of anterior part of the eye E photographed by the CCD camera 48 and the corneal reflexes of four light sources 41a to 41d are displayed on the TV monitor 6. Also, an alignment condition is detected according to the position of the corneal reflexes which is photographed by the CCD camera 48.

Electric system

Figure 3:
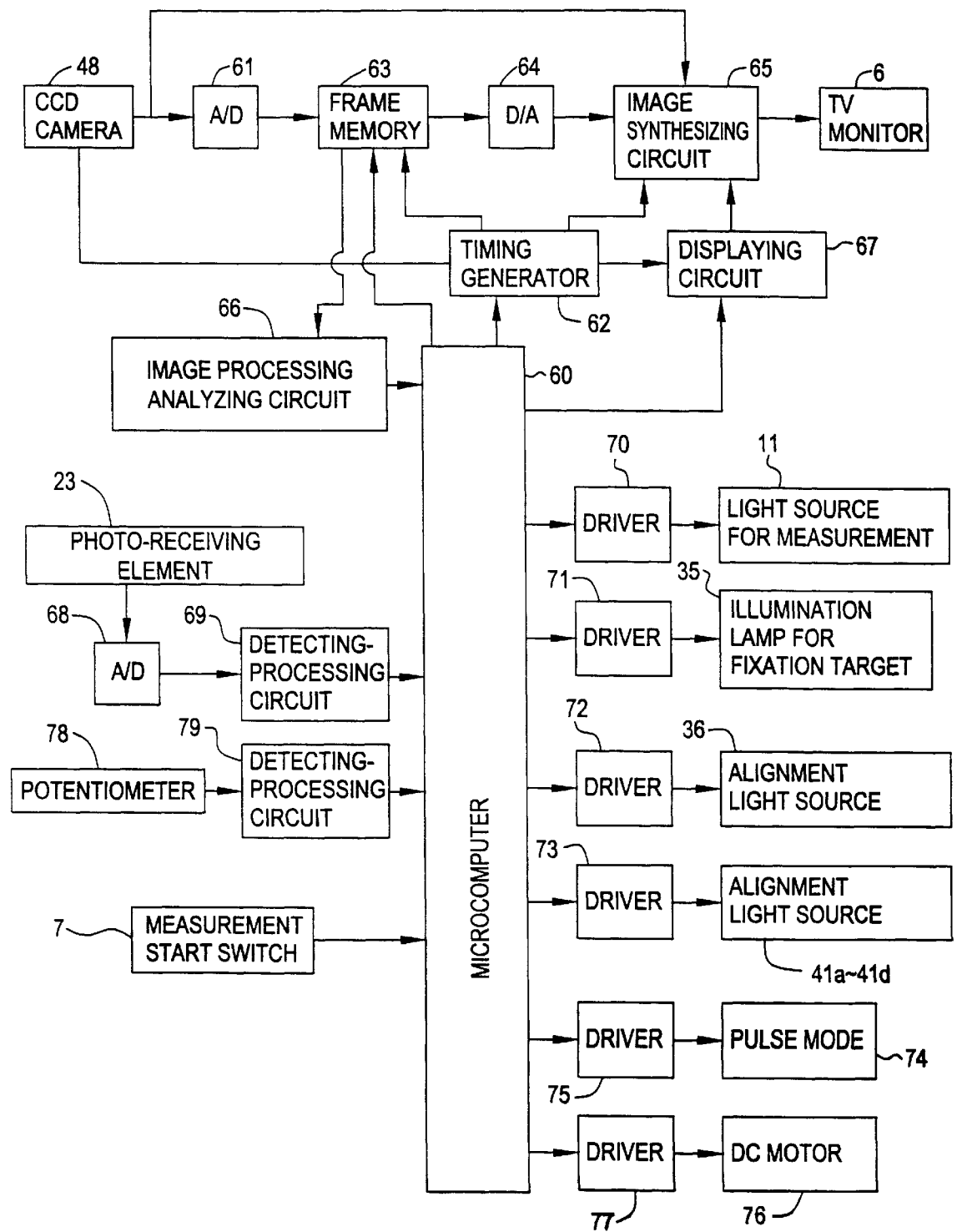
FIG. 3 is a view showing an important construction of a controlling system of an apparatus of the preferred embodiment of the present invention.

FIG. 3 shows an important part of a block diagram of an electric system of the apparatus of the preferred embodiment.

Video signal from the CCD camera 48 is digitized by A/D converter 61 then is captured by a frame memory 63 being synchronized with a signal of a timing generator 62. Image (Picture) captured by the frame memory 63 is displayed on the TV monitor 6 via D/A converter circuit 64 and an image synthesizing circuit 65 in real-time.

Reference numeral 66 is an image processing/analyzing circuit for analyzing the image captured by the frame memory 63 then detecting an alignment target image, a microcomputer 60 obtains coordinates of the target image based on the signal from the image processing/analyzing circuit 66.

Reference numeral 67 is a displaying circuit for generating an aim-mark, a figures a character information and the like which are displayed on the TV monitor 6, a signal from the displaying circuit 67 is synthesized with the image signal from the CCD camera 48 by an image synthesizing circuit 65, then is displayed on the TV monitor 6.

Also, the signal from the photo-receiving element 23 is digitized by A/D converter 68, then is given a predetermined processing by a detection processing circuit 69, and is inputted to the microcomputer 60.

Figure 4:
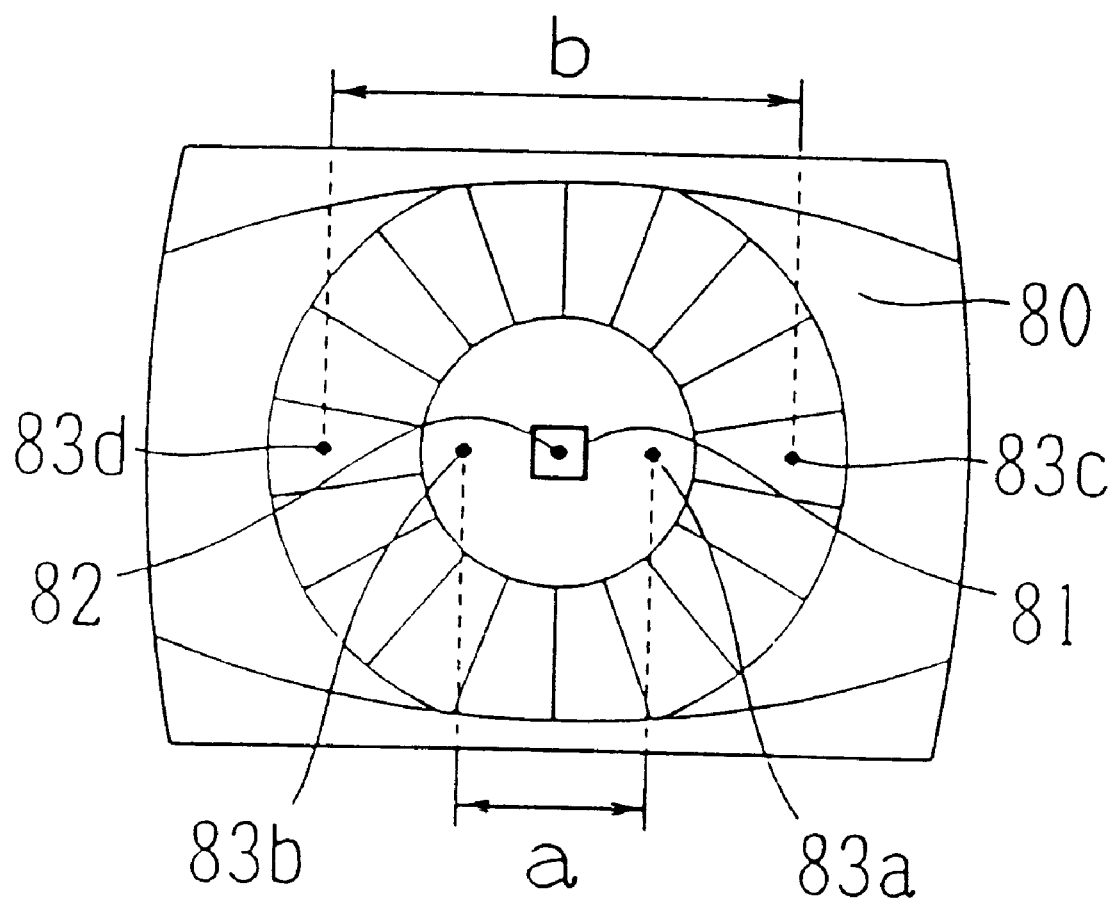
FIG. 4 is a view showing an example of an image (picture) in the case of an alignment.

Next, method for detecting an alignment condition of working distance will be described hereinafter. FIG. 4 is a view showing an example of an image of TV monitor 6 in the case that an alignment in lateral and vertical directions is completed. Reference numeral 80 is an image of an anterior part of the eye E, 81 is an aim-mark which is formed electrically (an aim-mark may be formed optically) 82 is a target image caused by corneal reflection of the light source 36 of the front target projecting optical systems 83*a* to 83*d* are target images caused by corneal reflection of respective point light sources 41*a* to 41*d* of the working distance target projecting optical system 40. The judgement for an alignment condition of working distance is performed based on a distance "a" between the target images 83*a* and 83*b*, and based on a distance "b" between the target images 83*c* and 83*d* (it may be performed based on deviation (distance) between the target image 82 and other respective target images).

Firstly, judgement for an alignment condition performed by the optical system of the preferred embodiment.

Figure 5:
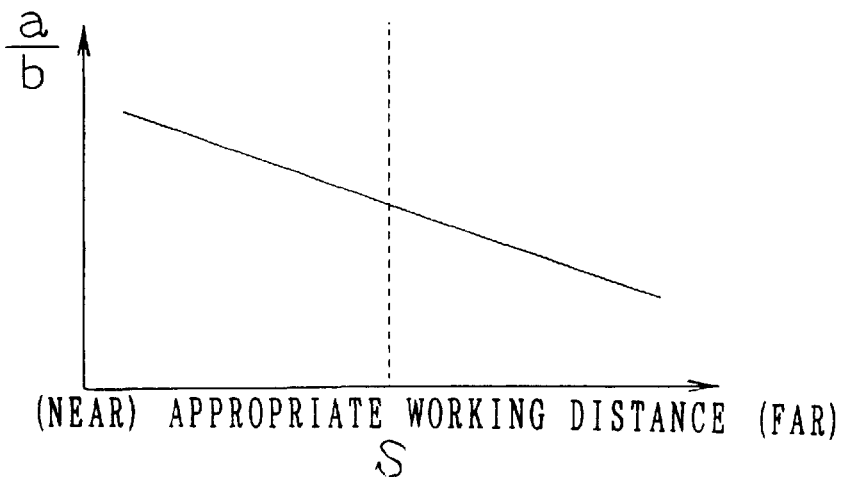
FIG. 5 is a view showing a graph of changing-ratio of the ratio of intervals between target images, which are projected with different angles.

The target images 83*c* and 83*d* are caused by the light sources 41*c* and 41*d* at an infinite-distance optically, therefore even if the apparatus is deviated to a direction of working distances then the distance "b" hardly changes. On the contrary, the target images 83*a* and 83*b* are caused by a divergent light bundle emitted by light sources 41*a* and 41*b* at a finite-distance optically, therefore the distance "a" between targets changes so as to be short (height of image becomes low) as a working distance between the eye E and the apparatus becomes longer. Therefore, the ratio "a" to "b" (a/b) changes as shown in FIG. 5, therefore an alignment condition can be judged by utilizing characteristics of this relationships. That is, if an appropriate working distance between the eye E and the apparatus is determined so as to be a/b=S (where S is a value having width which is determined based on the relationships to an alignment accuracy), then an alignment condition of working distance can be judged as follows.

(1) In the case of a/b>S, the apparatus is closer relative to the eye E.

(2) In the case of a/b=S, an adjustment of working distance is completed.

(3) In the case of a/b<S, the apparatus is further relative to the eye E.

Also, a deviation of working distance can be known by obtaining information of relationships between a deviation of working distance and the value of a/b as shown in FIG. 5 (causing a nonvolatile memory to store) in advance.

Next, such case will be described that the second target projecting optical systems 40*c* and 40*d* are made to project targets of finite-distance of which an optical distance in a direction of the axial line are the same by using a divergent light bundle, as the same as the first target projecting optical systems 40*a* and 40*b*.

Figure 6:
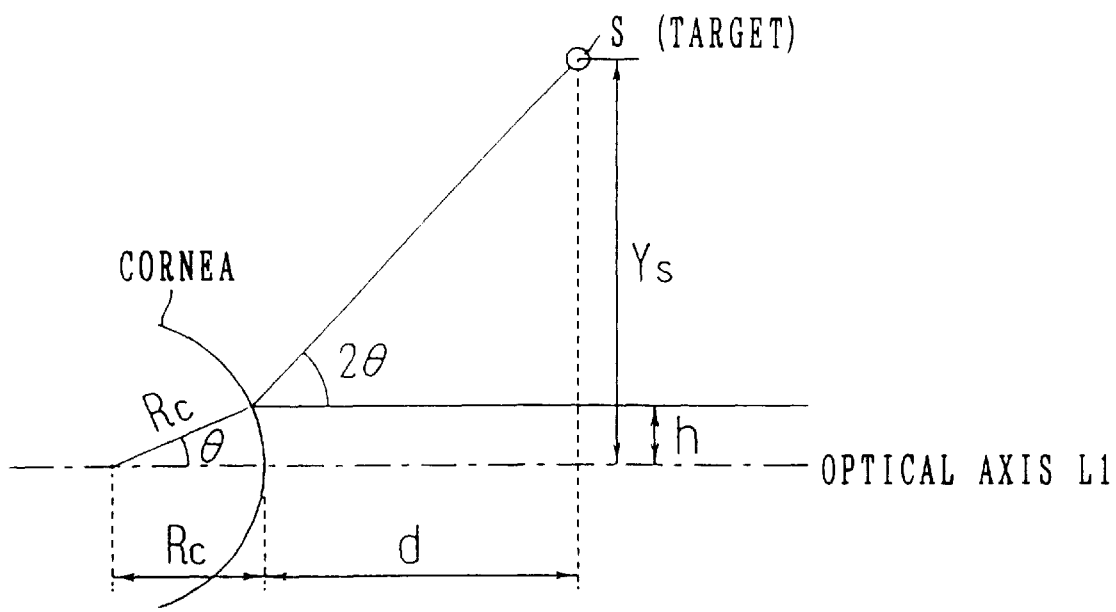
FIG. 6 is a view for illustrating a position where a target image is formed with respect to each distance from a light source and from a measuring optical axis.
Figure 7:
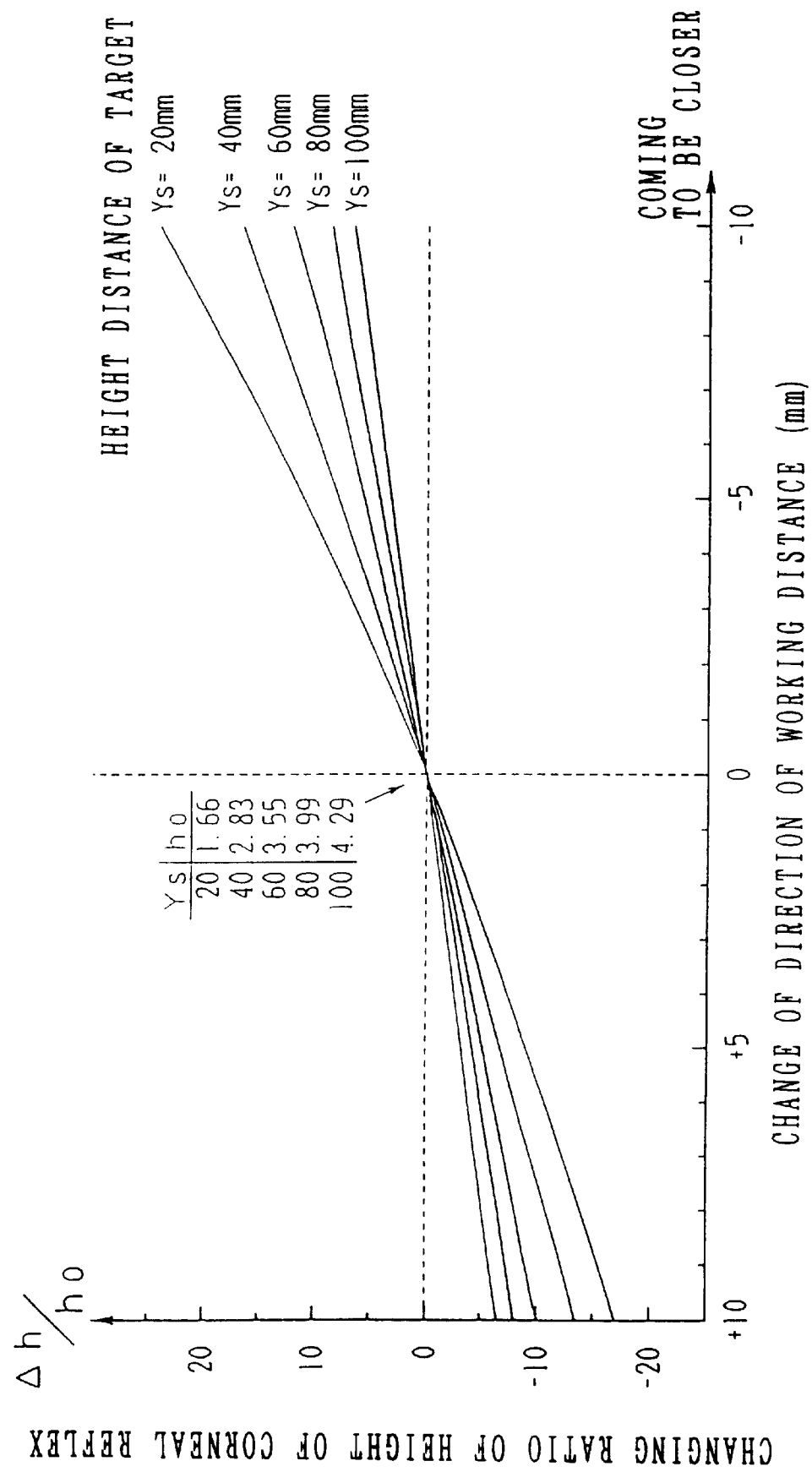
FIG. 7 is a view for illustrating change of a height of a target image in the case of projecting targets of finite distance of which optical distances are the same, with a divergent light bundle.

As shown in FIG. 6, a corneal radius is defined as Rc (=7.8 (mm)) a height distance from the optical axis L1 of the target (light source) S is defined as Ys, a height of corneal reflex of the target S is defined as h, and Ys is defined as to be changed 20 (mm) 40 (nm) 60 (mm) 80 (mm) and 100 (mm). FIG. 7 is a view thereupon showing relationships between the change (deviation) of a direction of working distance and the changing ratio of the height of corneal reflex (h/hO) (a height of corneal reflex is defined hO in the case that a distance "d" from the standard position to the target S in a direction of the optical axis L1 equals to the standard distance dO (=40 (mm)))

Referring to FIG. 7, as the height distance Ys of the target S is higher (as an angle made by the optical axis L1 and the projecting optical axis is larger) the changing ratio of the height of corneal reflex becomes smaller, and as the height distance Ys is shorter, the changing ratio of the height of corneal reflex becomes larger. Therefore, if configuration of the second target projecting optical systems 40*c* and 40*d* of the preferred embodiment are made to be the same as the first target projecting optical systems 40*a* and 40*b* (in the case of projecting the target by using a divergent light bundle) the ratio a/b changes as shown in FIG. 5 (provided that the slopes are different) Therefore, an alignment condition of working distance can be also judged as above-mentioned (1), (2) and (3).

Also, concerning respective targets of which a height from the measuring optical axis are different (the projecting angle are different) if the target projection on the inside is made to be closer to the optical axis as well as possible, and the target projection on the outside is made to be further from the optical axis as well as possible, then the difference between both changing ratios becomes larger, therefore the slope of graph a/b shown in FIG. 5 becomes larger, thereby the working distance detection can be performed sensible. However, if the target projection on the inside is made to be closer too much to the measuring optical axis, a height of corneal reflex relative to the optical axis L1 becomes lower, then the change of direction of working distance is difficult to be detected. Also, if the target projection on the outside is made to be further too much from the optical axis L1 then no corneal reflex can be obtained or the detecting error becomes larger caused by a non-spherical performance of cornea. Therefore, a distance arrangement of both targets is determined based on some conditions of the apparatus.

Next, the reason why the detection of working distance becomes easy by causing the optical distance of the target projection caused by the second target projecting optical system relative to the first target projecting optical system to be furthers will be described hereinafter.

Figure 8:
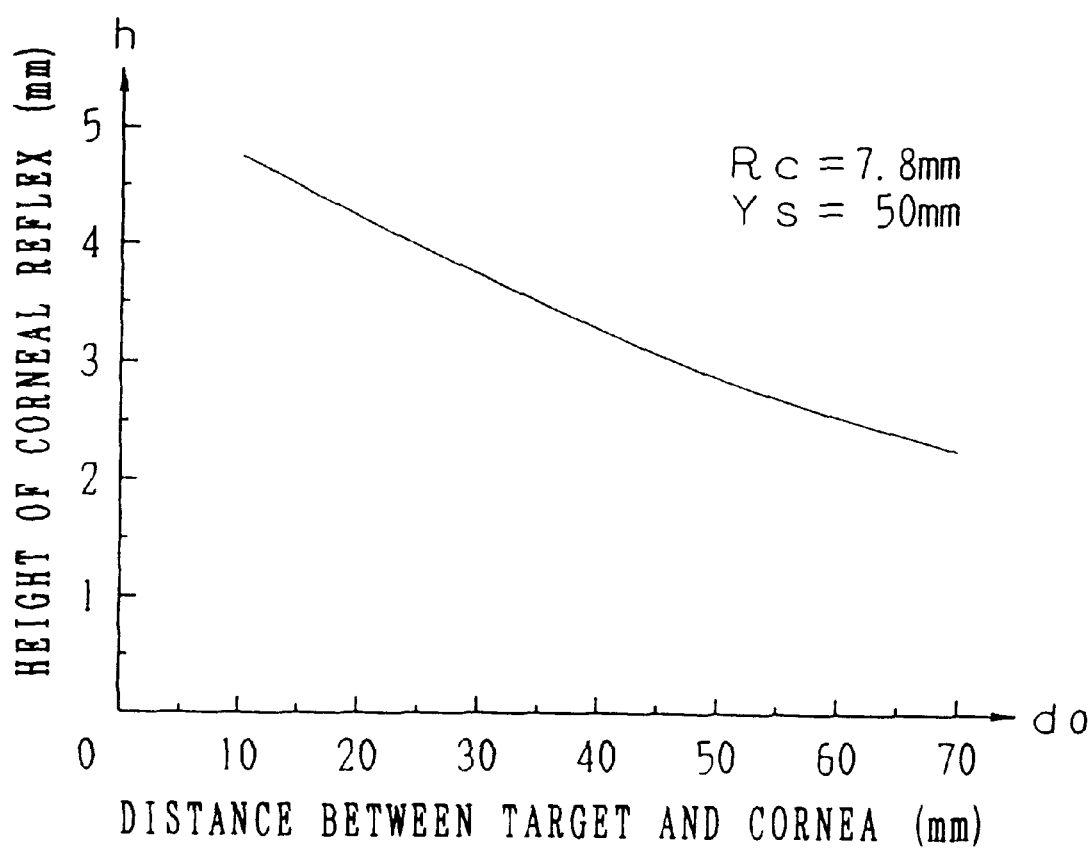
FIG. 8 is a view for illustrating detection of working distance in the case of causing optical distances of projecting target to be different.

In above-mentioned FIG. 6, under the condition that a height distance from the optical axis of the target is defined as Ys=50 (mm) an examiner makes an attempt to change the standard distance dO from the standard position to the target within a range of 10 (mm) to 70 (mm). Results for change of a height of the corneal reflex thereupon are shown in FIG. 8. Referring to the graph shown in FIG. 8, as the target S is closer to the eye E in a direction of an axis lines a changing state of a height of the corneal reflex (a differential value of graph) becomes larger. Therefore, according to relationships between its result and the height of the target arrangement mentioned above, if the optical distance of the inside target relative to the outside targets is made to be closer to the eye E, then the change of a height of the corneal reflex (distance "a") relative to the deviation of working distance becomes larger, thereby the slope of graph a/b shown in FIG. 5 becomes larger, allowing the detection of working distance to become easier. Also, the detection of working distance becomes easier by making the change of a height of the corneal reflex of the target disposed outside (distance "b") relative to the deviation of working distance to be smaller, too. That is, it may be suitable that the target distance caused by the first target projecting optical system of inside is made to be shorter, and on the contrary the target distance caused by the second target projecting optical system of outside is made to be longer. The second target projecting optical system allows that a target is placed at an infinite distance as shown in FIG. 2 by using a collimating lens (in addition, if it is made that the first target projecting optical system projects the target of infinite-distance, then the target images relative to the working distance for both hardly change, therefore at least the one between them is made to projects the target of a finite distance optically).

Further, if a light is made to be a converging light by disposing a collecting lens in the second target projecting optical system instead of the collimating lens, then the change of the distance "b" relative to the working distance shown in FIG. 4 becomes opposite to the change of the distance "a" therefore the slope of graph a/b becomes larger, thereby the detection of working distance becomes easier. However, if a converging light is adopted, then the detecting area is made to be narrow, such consideration is needed that causing the aperture of the collecting lens to be large or eliminating the aberration influence or the like.

Next, the operation of the apparatus having such composition as described above will be described hereinafter. The examiner places the eye E at a predetermined position by using the chin rest 2, then turns on respective light sources. Then an anterior image of the eye E illuminated by the point light sources 41a to 41d and corneal reflexes caused by the light sources 36 and 41a to 41d by respective target projecting optical systems are captured by the CCD camera 48, then are displayed on the TV monitor 6. The examiner performs the alignment adjustment so that the target image 82, which is positioned at approximately the center of the image 80 of the anterior part of the eye E, may enter in the aim-mark 81 by moving the body 3 in forward and backward directions and a lateral direction by operating the joystick 5 and by moving the measuring part 4 in a vertical direction relative to the body 3 by operating the rotation knob 5a with observing the TV monitor 6. The microcomputer 60 extracts the target image 82, positioned at the center, among five detected target images which are detected based on signals from the image processing/analyzing circuit 66, and calculates the position of the target image 82, then detects an alignment condition of vertical and lateral directions of the measuring part 4 (the measuring optical system) relative to the eye E; and obtains the deviation of the target images from the optical axis. Besides, the alignment detection in vertical and lateral directions can be performed by calculating the center coordinates based on the positions of the target images 83a to 83d, and by obtaining the deviation information based on a position of center coordinates relative to the measuring optical axis without providing the front target projecting optical system.

Figure 9:
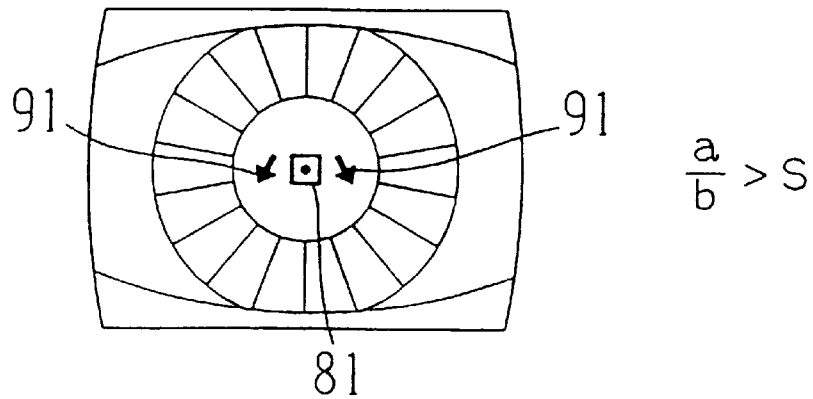
FIG. 9($a$)–9($c$) is a view showing an example of an indicator displayed on TV monitor, which indicates a direction where a body should be moved in a direction of working distance.
Figure 9:
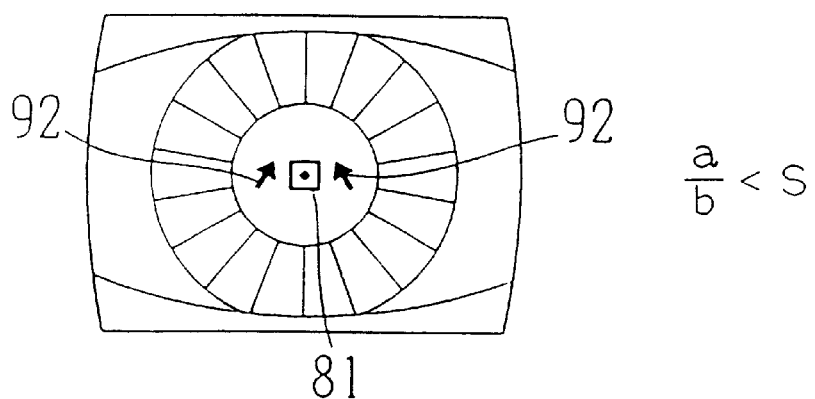
Figure 9:
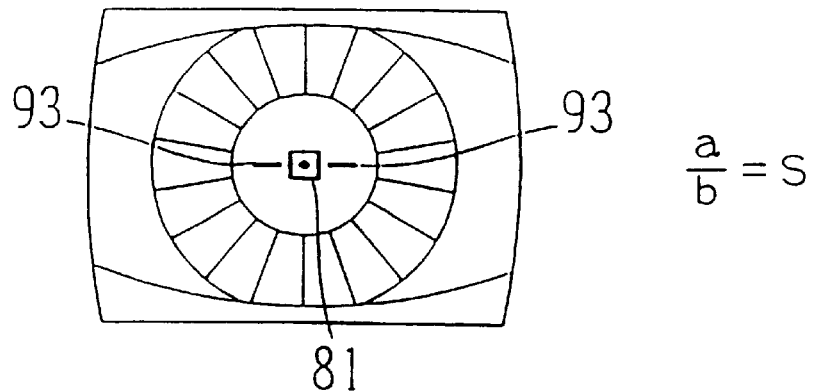
Figure 10:
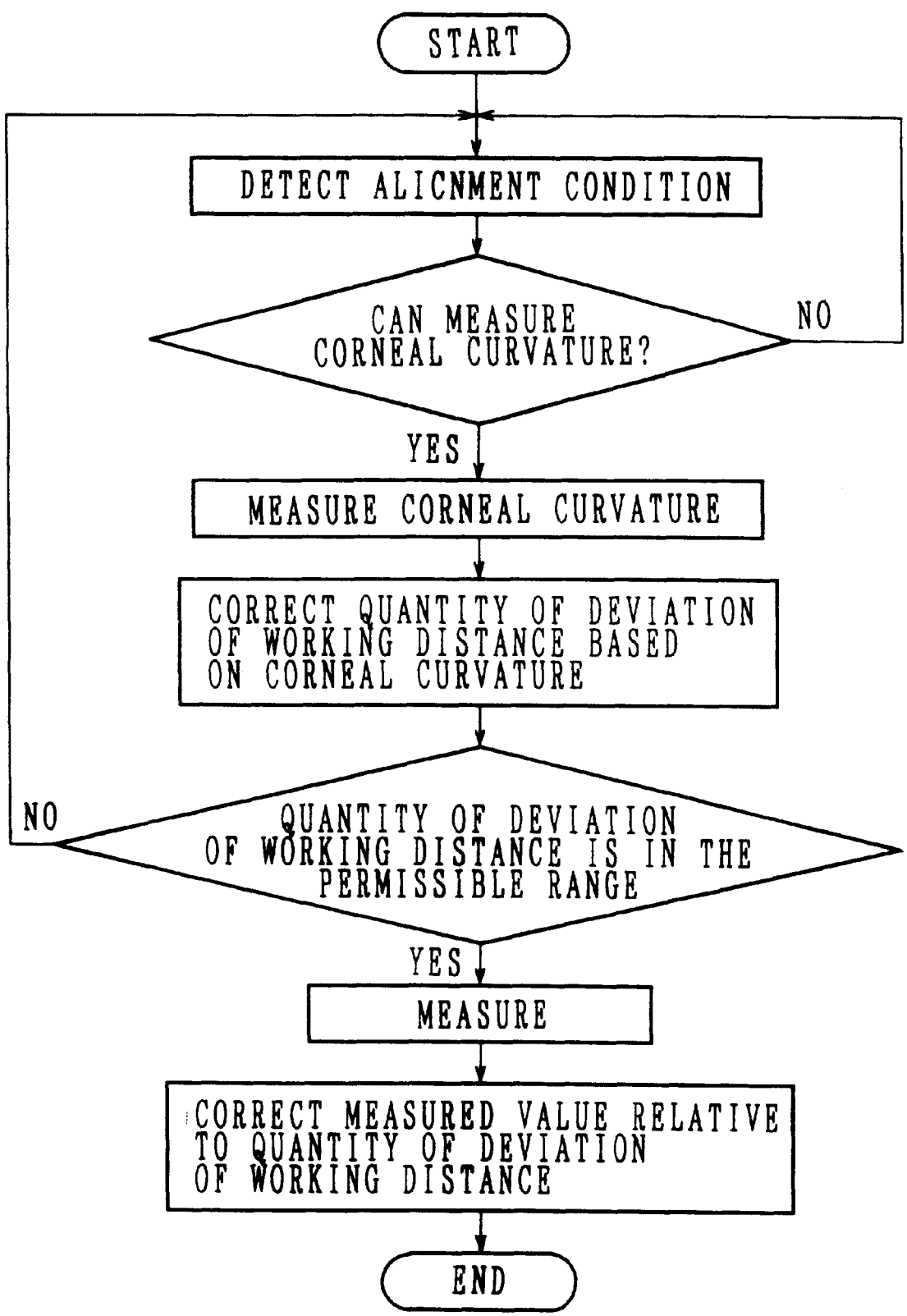
FIG. 10 is a flowchart for describing a routine procedure of correction of a measured value and a quantity of deviation of alignment.

If the target image 82 (or positions of center coordinates of the target images 83a to 83d) enters a predetermined permissible area (range), then the apparatus detects the target images caused by the working distance target projecting optical system 40, thereby obtains information of an alignment condition of working distance by above-mentioned method. The microcomputer 60 gives the displaying circuit 67 instructions based on information of an alignment condition of working distances and the indicators which informs the examiner of a direction where the measuring part 4 should be moved, is displayed on the TV monitor 6 FIG. 9 is an example of display. (a) shows the case that the apparatus is closer relative to the eye E, referring to figures an indicator 91 denoted by oblique-lower arrows is displayed at just by both sides of the aim-mark 81, meaning that the measuring part 4 together with the body 3 are to be moved to further direction (examiner s direction) relative to the eye E. (b) shows the case that the apparatus is further relative to the eye E, an indicator 92 denoted by oblique-higher arrows is displayed at just by both side of the aim-mark 81, meaning that the measuring part 4 together with the body 3 are to be moved closer direction (examinee's direction) relative to the eye E. (c) shows the case that a positional adjustment of working distance is completed, an indicator 93 denoted by line-bar is displayed at just by both sides of the aim-mark 81.

The examiner causes the body 3 to move in forward and backward directions by operating the joystick 5 with complying the indication of alignment of working distance mentioned above, thereby an alignment adjustment in a direction of working distance is made to be completed.

After the microcomputer 60 judges that an alignment in working distance is completed and confirms that an alignment condition in vertical and lateral directions is in a predetermined permissible ranges then the microcomputer 60 executes measurement by giving a measurement starting signal automatically (It is displayed on the TV monitor 6 or is informed of the examiner by sound that the alignment is completed, based on this, the measurement may be executed by depressing the starting-switch 7 for measurement) The target image is projected onto the fundus of the eye E by turning on the light source 11s for measurement, then the target image reflected by the fundus is detected by the photo-receiving element 23. The moving lens 21 and the target plate 13 are moved to the position where is conjugate with the fundus based on the signal from the photo-receiving element 23. Next, after the fixation target 33 and the fundus of the eye E are placed at the conjugate position by moving the first relay lens 31, further the first relay lens 31 is made to move so as to be fogged appropriate quantity of diopter. The light source 11s for measurement, the corneal reflection eliminating mask 20 and the photo-receiving element 23 are made to rotate with the center at the optical axis under the condition that the eye E is fogged. While rotating, the target plate 13 and the moving lens 21 are moved based on signals from the photo-receiving element 23 and the potentiometer 78 detects the quantity of movement thereof, calculating a value of the refractive power in respective meridian directions. The microcomputer 60 gives a predetermined processing to the value of the refractive power, then obtains the refractive power of the eye E. The measured result is displayed on the TV monitor 6.

Besides, in the case of measurement (particularly, in the case that the measurement is executed by depressing the starting switch 7 for measurement by the examiner.), even though an alignment in working distance is not completed strictly, a quantity of deviation of working distance is obtained as mentioned above, the measured value may be corrected based on the quantity of deviation. The correction for measured value of refractive power can be performed as follows. If a value of refractive power obtained by the measurement is defined as Dx (diopter) a quantity of deviation of working distance upon measurement relative to the appropriate working distance is defined as x (m), and a true value of refractive power is defined as D (diopter), then D is expressed by following expression:

$$D=1/[(1/Dx)-x],$$

thereby a corrected value of refractive power can be obtained.

The alignment operation as mentioned above is performed by manual operation by the examiners instead of this, the moving mechanism which moves electrically to respective directions or directions in part by driving a motor, thereby an alignment adjustment may be performed automatically based on the detected result of an alignment condition. Also, in the preferred embodiments the description is made by making a point of setting type apparatus, the present invention is applied to the hand-held type apparatus similar to the setting type apparatus.

Referring to above-mentioned embodiments, the target images are formed on the same one line by disposing the alignment light sources on the same meridian which passes through the corneal vertex in order to minimize influence caused by astigmatism of eye E, however, if the curvature changes little, a working distance can be detected without disposing on the same meridian.

As is described above, since judgement for an alignment condition of working distance is performed based on the ratio of the height of the target image (corneal reflex) by the first target projecting optical system to the height of the target image by the second target projecting optical system (a/b) it can be performed precisely without being influenced by individual difference of corneal curvature radius. However, this method for detection is depends on a corneal curvature radius to some extent, therefore it includes an error a little in a strict sense of the word. The error of detection caused by difference of a corneal curvature radius is can be obtained as follows. As described above, the second target projecting optical systems 40c and 40d project targets of infinite distance with a projecting optical axis having a predetermined axis, therefore the height of the target image does not change hardly, even if a direction of working distance is deviated. Therefore, a corneal curvature radius can be obtained by detecting the height of target image. Next, by calculating a quantity of deviation between the obtained corneal curvature radius and a standard corneal curvature radius, an error of working distance is obtained based on the quantity of deviation. Thereby, the alignment can be performed more precisely by correcting information of an alignment condition. Also, the measured value obtained by executing the measurement may be corrected by adding an error of working distance.

The present invention may be embodied in other specific forms without departing from the spirit or essential characteristics thereof. For instance, in above embodiment, the light sources for projecting the target of working distance are four, however, if at least a pair of targets of which respective distances from the measurement optical axis is different is projected onto the eye E and the height of the corneal reflex is calculated based on the deviation from the optical axis for measurement, then the working distance can be detected similar to the detection of the above-mentioned embodiment.

Also, the target for detecting a working distance may be realized in other way that projects the ring image at outside of the optical axis from oblique direction or that projects the slit images of which the height distance being different from the optical axis. In these cases, after the target image is detected by using the two dimensional positional detecting element, an image in specified direction is extracted by giving the image processing then it is utilized for detecting a working distance similar to above-mentioned description.

The embodiment is described by making the point of the refractive power measuring apparatus the present invention is applied for many kinds of ophthalmic apparatus which needs that the eye E has a predetermined relationships with the measuring system the inspecting system or the like.

For example, referring to an corneal shape measuring apparatus the same device as the second target projecting optical systems 40c and 40d, which are used in the working distance target projecting optical system of the preferred embodiment, is placed at the position where is made to be rotated 90 degrees then in the case of measurement, the second target projecting optical system is also served as the target projecting optical system for measuring the shape of cornea.

Upon measurement, if at least three target images which are projected onto the cornea are detected as cited in Japanese Patent Laid open SHO61-85902 and the like then the corneal shape can be calculated.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention The embodiments chosen and described in order to explain the principles of the invention and its practical application to enable one skilled in the art to utilize the invention in various embodiments and with various modifications as are suited to the particular use contemplated It is intended that the scope of the invention be defined by the claims appended hereto, and their equivalents

What is claimed is:

1. An alignment detecting apparatus for detecting an alignment condition between an eye to be examined having such reflecting surface that is approximately spherical surface or approximately toric surface and a device having a standard axial line, the apparatus comprising:

a target projecting optical system which includes a first target projecting optical system for projecting a first target with a predetermined angle relative to said standard axial line and a second target projecting optical system for projecting a second target with a different angle compared with the angle of said first target projecting optical system relative to said standard axial line, of which at least one between said first and second targets is a target of a finite distance;

a detecting optical system for detecting positions of images of said first and second targets which are projected onto the eye by said first and second target projecting optical systems; and a judging means for judging the alignment condition based on results detected by said detecting optical system.

2. The alignment detecting apparatus according to claim 1, wherein said first target projecting optical system projects the first target of an infinite distance optically; and said second target projecting optical system projects the second target of a predetermined finite distance optically, whereby the alignment condition in a direction of said standard axial line is judged by said judging means based on the ratio of a height of the first target image to a height of the second target image, which are detected.

3. The alignment detecting apparatus according to claim 2 wherein said first and second target projecting optical systems comprise two projecting optical systems respectively which are disposed so as to be symmetric with respect to said standard axial line.

4. The alignment detecting apparatus according to claim 3 wherein said judging means calculates a center of at least one between said first and second target images which are detected and then judges the alignment condition of a plane intersecting at right angles relative to said standard axial line based on said center, and then judges the alignment condition in a direction of said standard axial line based on a ratio of a height of said first target image and a height of said second target image.

5. The alignment detecting apparatus according to claim 2, further comprising a third target projecting optical system for projecting a third target from a direction of said standard axial line, whereby a image of the third target which is projected onto the eye by said third target projecting optical system is detected by said detecting optical system and the alignment condition of a plane intersecting at right angles relative to said standard axial line is judged by said judging means based on a position of the third target image which is detected.

6. The alignment detecting apparatus according to claim 2, wherein said first and second target projecting optical systems project respective targets onto approximately same meridian of the surface of the eye.

7. The alignment detecting apparatus according to claim 2, further comprising:

displaying means for displaying information of the alignment condition judged by said judging means.

8. The alignment detecting apparatus according to claim 2, further comprising:

a moving means for moving the apparatus relatively with respect to the eye; and a control means for controlling the drive of said moving means based on information of the alignment condition judged by said judging means.

9. The alignment detecting apparatus according to claim 2, further comprising:

alignment correcting means for correcting the alignment condition in a direction of said standard axial line based on detected result of said first target image.

10. The alignment detecting apparatus according to claim 2, wherein said standard axial line is an optical axis of a measuring optical system, and the apparatus comprises a measured result correcting means for correcting results measured by said measuring optical system based on the alignment condition in a direction of said standard axial line.

11. The alignment detecting apparatus according to claim 1, wherein said first target projecting optical system projects the first target with a converging light; and said second target projecting optical system projects the second target of a predetermined finite distance optically, whereby the alignment condition in a direction of said standard axial line is judged by said judging means based on the ratio of a height of the first target image to a height of the second target image which are detected.

12. The alignment detecting apparatus according to claim 11, wherein said first and second target projecting optical systems comprise two projecting optical systems respectively which are disposed so as to be symmetric with respect to said standard axial line.

13. The alignment detecting apparatus according to claim 12, wherein said judging means calculates a center of at least one between said first and second target images, which are detected and then judges the alignment condition of a plane intersecting at right angles relative to said standard axial line based on said center, and then judges the alignment condition in a direction of said standard axial line based on a ratio of a height of said first target image and a height of said second target image.

14. The alignment detecting apparatus according to claim 11, further comprising a third target projecting optical system for projecting a third target from a direction of said standard axial line, whereby a image of the third target which is projected onto the eye by said third target projecting optical system is detected by said detecting optical system, and the alignment condition of a plane intersecting at right angles relative to said standard axial line is judged by said judging means based on a position of the third target image which is detected.

15. The alignment detecting apparatus according to claim 11, wherein said first and second target projecting optical systems project respective targets onto approximately same meridian of the surface of the eye.

16. The alignment detecting apparatus according to claim 11, further comprising:

a displaying means for displaying information of the alignment condition judged by said judging means.

17. The alignment detecting apparatus according to claim 11, further comprising:

a moving means for moving the apparatus relatively with respect to the eye; and a control means for controlling the drive of said moving means based on information of the alignment condition judged by said judging means.

18. The alignment detecting apparatus according to claim 11, wherein said standard axial line is an optical axis of a measuring optical system, and the apparatus comprises a measured result correcting means for correcting result measured by said measured optical system based on the alignment condition in a direction of said standard axial line.

19. The alignment detecting apparatus according to claim 1, wherein said first and second target projecting optical systems comprise two projecting optical systems respectively which are disposed so as to be symmetric with respect to said standard axial line.

20. The alignment detecting apparatus according to claim 19, wherein said judging means calculates a center of at least one between said first and second target images, which are detected, and then judges the alignment condition of a plane intersecting at right angles relative to said standard axial line based on said center, and then judges the alignment condition in a direction of said standard axial line based on the ratio of a height of said first target image and a height of said second target image.

21. The alignment detecting apparatus according to claim 1, further comprising a third target projecting optical system for projecting a third target from a direction of said standard axial line, whereby a image of the third target which is projected onto the eye by said third target projecting optical system is detected by said detecting optical system and the alignment condition of a plane intersecting at right angles relative to said standard axial line is judged by said judging means based on a position of the third target image which is detected.

22. The alignment detecting apparatus according to claim 1, wherein said first and second target projecting optical systems project respective targets onto approximately same meridian of the surface of the eye.

23. The alignment detecting apparatus according to claim 1, further comprising a displaying means for displaying information of the alignment condition judged by said judging means.

24. The alignment detecting apparatus according to claim 1, further comprising:

a moving means for moving the apparatus relatively with respect to the eye; and a control means for controlling the drive of said moving means based on information of the alignment condition judged by said judging means.

25. The alignment detecting apparatus according to claim 1, wherein said standard axial line is an optical axis of a measuring optical system, and the apparatus comprises a measured result correcting means for correcting results measured by said measuring optical system based on the alignment condition in a direction of said standard axial line.

* * * * *